United States Patent [19]

Heindl et al.

[11] Patent Number: 4,995,856
[45] Date of Patent: Feb. 26, 1991

[54] VENTRICULOSTOMY RESERVOIR

[75] Inventors: Alfons Heindl; Stephen W. Laguette, both of Goleta; Leanne M. Lintula, Santa Barbara, all of Calif.

[73] Assignee: Pudenz-Schulte Medical Research Corporation, Goleta, Calif.

[21] Appl. No.: 365,906

[22] Filed: Jun. 14, 1989

[51] Int. Cl.⁵ ............................................. A61M 5/00
[52] U.S. Cl. ......................................... 604/8; 604/9
[58] Field of Search ................... 604/8, 9, 10, 27, 33, 604/247, 249; 137/508

[56] References Cited

U.S. PATENT DOCUMENTS

| | | | |
|---|---|---|---|
| 3,111,125 | 11/1963 | Schulte | 604/9 |
| 3,503,402 | 3/1970 | Schulte | |
| 4,321,923 | 3/1982 | Nichols | 604/249 |
| 4,471,942 | 9/1984 | Kocanowski | 604/33 |
| 4,560,375 | 12/1985 | Schulte et al. | 604/9 |
| 4,636,194 | 1/1987 | Schulte et al. | 604/9 |
| 4,787,887 | 11/1988 | Saenz Arroyo | 604/9 |

OTHER PUBLICATIONS

Copy of "The Complete Line of Neurosurgery Shunting Products," American Heyer-Schulte (19 pages).
Copy of "Codman Holter Valve System, Hydrocephalus Shunt Systems," (1981) (22 pages).
Pp. 13, 14 and 15 from the "CSF-Ventriculostomy Reservoirs Catalog," for Pudenz-Schulte Medical Research Corporation.
Copy of "Ventricular Access Devices" for Pudenz-Schulte Medical Research Corporation (12 pages).

Primary Examiner—Robert A. Hafer
Assistant Examiner—Kerry Owens
Attorney, Agent, or Firm—Kelly, Bauersfeld & Lowry

[57] ABSTRACT

A ventriculostomy reservoir includes a rigid base and an elastomeric cap which is positioned over the base to enclose a reservoir well. A rigid cap insert is captured by the lower portion of the cap and is positioned for engagement with the base. The cap insert and the base are configured so that the cap may be snap-fit onto the base in a manner forming a fluid-tight seal therebetween. In one form of the invention, the cap insert includes a cylindrical portion which extends downwardly from a flange-like portion captured within the cap, to fit within an upwardly extending wall portion of the base. The cylindrical portion includes an encircling protrusion on an exterior surface thereof which engages and fits within an encircling detent provided on the interior surface of the wall portion to snap-fit the cap to the base. In a second embodiment of the invention the cap insert exteriorly surrounds an upper end of the base, and a similar protrusion and detent arrangement is utilized to snap-fit the cap to the base. In a third embodiment of the invention the cap insert overlies an upper end of the base and is secured to the base through an interference fit both on interior and exterior surfaces of the wall portion of the base.

35 Claims, 3 Drawing Sheets

VENTRICULOSTOMY RESERVOIR

BACKGROUND OF THE INVENTION

This invention relates generally to surgically implantable valves. More particularly, this invention relates to devices for the drainage of cerebrospinal fluid from the ventricle of the brain and for monitoring such drainage.

As is well known in the medical arts, to relieve undesirable accumulation of fluids, it is frequently necessary to provide a means for draining a fluid from one part of the human body to another in a controlled manner. This is required, for example, in the treatment of hydrocephalus, an ailment usually afflicting infants or children in which fluids which ought to drain away accumulate within the skull and thereby exert extreme pressure and skull deforming forces.

In treating hydrocephalus, cerebrospinal fluid accumulated in the brain ventricles is drained away by a catheter inserted into the ventricle through the skull. The catheter is connected to a conduit which conducts the fluid away from the brain to be reintroduced into the vascular system, as by extending through the patient's jugular vein to the atrium portion of the heart. To control the flow of cerebrospinal fluid and maintain the proper pressure in the brain ventricle, a pump or valve is placed in the conduit between the brain and the heart atrium. Examples of such pump and valve devices are shown in U.S. Pat. No. 4,560,375, to Schulte et al.

Ventriculostomy reservoirs are often utilized in connection with such pumps or valves to provide a convenient location for sampling accumulated cerebrospinal fluid as close to the brain ventricles as possible. Such ventriculostomy reservoirs may be placed over a burr hole through the skull to facilitate sampling of cerebrospinal fluid before the implantation of the fluid conduit.

Prior ventriculostomy reservoirs typically include a metal base having a catheter connector, an integral, upwardly extending cylindrical wall portion, and a flange portion integrally formed with and overlying the wall portion. A cap made of a silicone elastomer material is typically provided to enclose the upper end of the base and define, with the base, an internal reservoir. The cap usually includes an annular internal recess configured to fit over the flange portion of the base.

The cap and the base of such prior ventriculostomy reservoirs are usually separated prior to implantation. The surgeon, after drilling a burr hole through the skull, attaches a catheter to the connector at the lower end of the base, and then positions the base on the skull. Previously, the surgeon has then been required to grasp the cap and stretch its peripheral edges over the upper flange of the base to position the flange within the recess of the cap. This has, however, presented difficulties for the surgeon which the present invention eliminates.

More particularly, during an operation the surgeon's gloves usually become quite slippery due to contact with blood and other body fluids. This often makes the grasping of objects difficult, particularly when the objects are very small. The caps of prior ventriculostomy reservoirs also tend to become slippery and difficult to handle when they have come in contact with body fluids. This has made it difficult for surgeons to quickly and efficiently grasp and stretch the cap over the upper flange of the base.

Accordingly, there has been a need for a convenient means for attaching the cap of a ventriculostomy reservoir to the base, which renders the device relatively inexpensive to manufacture and which can be constructed substantially of non-metallic parts. Such a device would preferably suffer no degradation in operation within a patient in comparison with prior ventriculostomy reservoirs, and eliminate, as much as possible, handling of the cap separately from the base. In this regard it would be desirable to provide means for connecting the cap to the base in a manner providing a fluid-tight seal therebetween, which required nothing more than for the surgeon to push the cap onto the base at an appropriate time during the surgical procedure. As will become apparent from the following description, the present invention satisfies these needs and provides other related advantages.

SUMMARY OF THE INVENTION

The present invention resides in a ventriculostomy reservoir having improved assembly characteristics, and which fulfills each of the needs set forth above. The improved ventriculostomy reservoir comprises, generally, a base configured to provide an internal reservoir well, and a cap which is positioned over the base to enclose the reservoir well. The base includes an inlet and an upwardly extending wall portion integrally formed with the inlet, and the cap includes a dome portion and an outlet for the reservoir. Means are provided for attaching the cap to the base to form a fluid-tight fit therebetween.

The attaching means includes a first means associated with the base for connecting the base to the cap, and a second means associated with the cap for connecting the base to the cap. The first and second connecting means cooperate with one another to form an interference fit which prevents fluid leakage. In forming this interference fit, the first and second connecting means may include a detent provided in one of the first and second connecting means, and a protrusion provided on the other of the first and second connecting means, wherein the detent and the protrusion snap-fit together to securely hold the cap to the base.

In a preferred form of the invention, the base is formed of a rigid material such as polypropylene, and is configured to provide an internal reservoir well. This base includes a catheter connector defining a reservoir inlet, and the wall portion is integrally formed with the catheter connector and extends upwardly therefrom.

The cap is preferably constructed of an elastomeric material and is placed over the base to enclose the reservoir well and define, with the base, an internal reservoir. The cap includes a peripheral supporting portion formed integrally with the dome portion, and an outlet arm which defines an outlet channel. The outlet arm is integrally formed with the dome. Reinforced sheeting is attached to the dome peripheral supporting portion in order to minimize elastic stretching of a lower surface of the dome.

A rigid cap insert is securely affixed to the cap and is positioned for engagement with the base. The cap insert includes an annular flange-like portion which is attached to the dome peripheral supporting portion. The annular flange-like portion of the cap insert includes a plurality of apertures filled with an adhesive which tends to secure the cap insert to the dome peripheral supporting portion.

In one illustrated embodiment, the base includes a flange portion integrally formed with and overlying the wall portion, which flange portion includes an upper planar surface. The dome includes a lower sealing surface which lies against the upper planar surface of the flange portion of the base. The cap insert includes a cylindrical portion which extends downwardly from the annular flange-like portion, and this downwardly extending cylindrical portion fits within the upwardly extending wall portion of the base. The first connecting means includes an encircling detent on an interior surface of the wall portion of the base, which is adjacent to the cylindrical portion of the cap insert. The second connecting means includes an encircling protrusion on an exterior surface of the cylindrical portion of the cap insert. Engagement between the protrusion and the detent connects the cap to the base and forms a fluid-tight seal therebetween.

In a second illustrated embodiment, the annular flange-like portion of the cap insert is captured within the dome peripheral supporting portion to exteriorly surround an upper end of the base. In this embodiment, the first connecting means includes an encircling detent on an exterior surface of the wall portion of the base which is adjacent to and surrounded by the cap insert. The second connecting means includes an encircling protrusion which extends inwardly from the annular flange-like portion of the cap insert. Again, the engagement between the protrusion and the detent connects the cap to the base and forms a fluid-tight seal therebetween.

In a third illustrated embodiment, the annular flange-like portion of the cap insert is attached to the dome peripheral supporting portion to exteriorly surround an upper end of the base. In this embodiment, the base includes a flange portion integrally formed with and overlying the wall portion, and the cap insert is configured to exteriorly surround the base flange. The cap insert is provided a detent which receives the outer periphery of the base flange, and the cap insert further overlies the base flange and includes means extending into the reservoir well for engaging an interior surface of the wall portion of the base in an interference fit.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
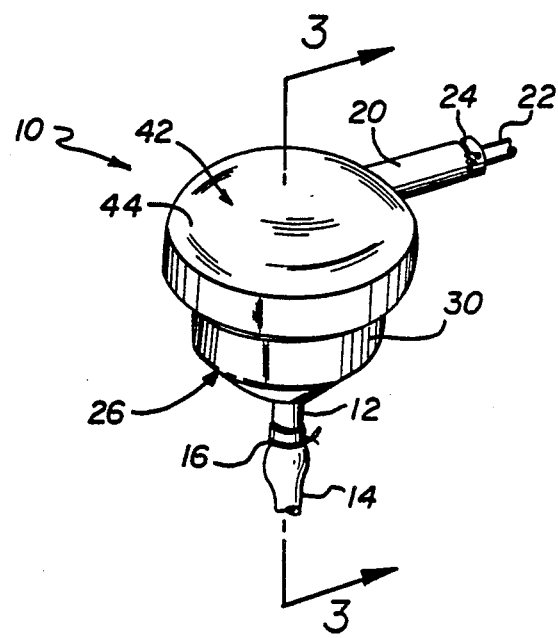
FIG. 1 is a perspective view of one preferred form of a ventriculostomy reservoir embodying the invention, illustrated with an upper outlet tube connected to a straight connector, and with a lower inlet connector engaged by a catheter.
Figure 2:
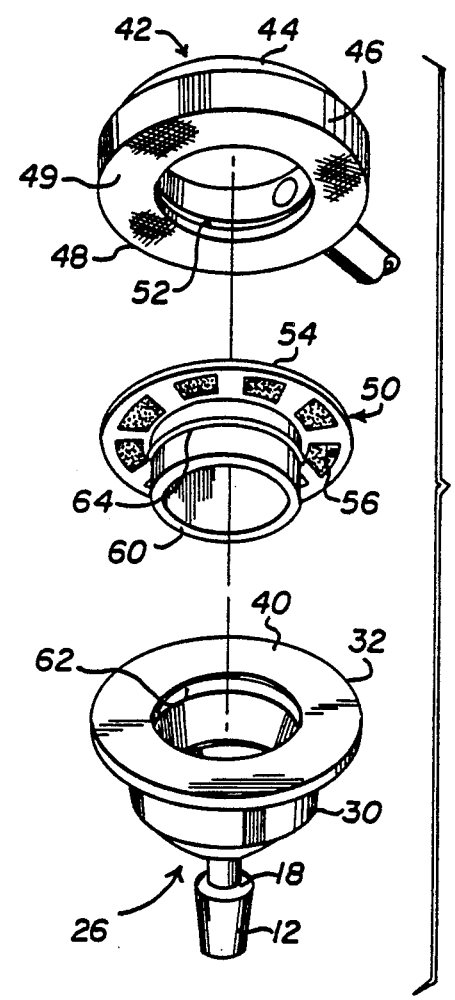
FIG. 2 is an enlarged exploded perspective view of the ventriculostomy reservoir illustrated in FIG. 1, illustrating the relationship of the three primary components thereof.
Figure 5:
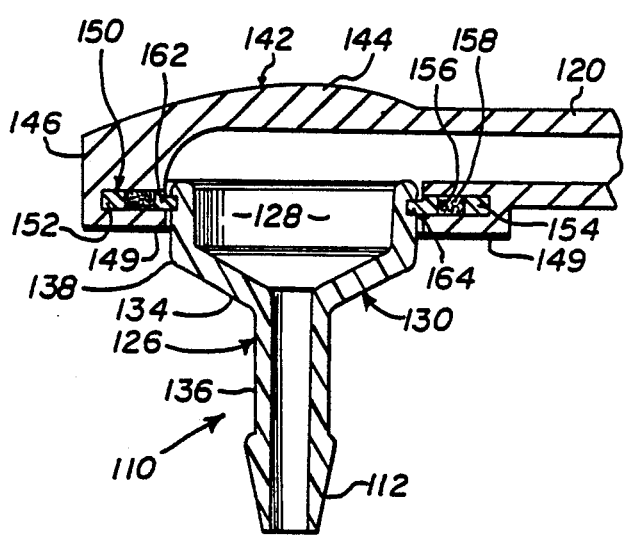
FIG. 5 is a vertical sectional view similar to FIG. 4, of second embodiment of the ventriculostomy reservoir of the present invention.
Figure 3:
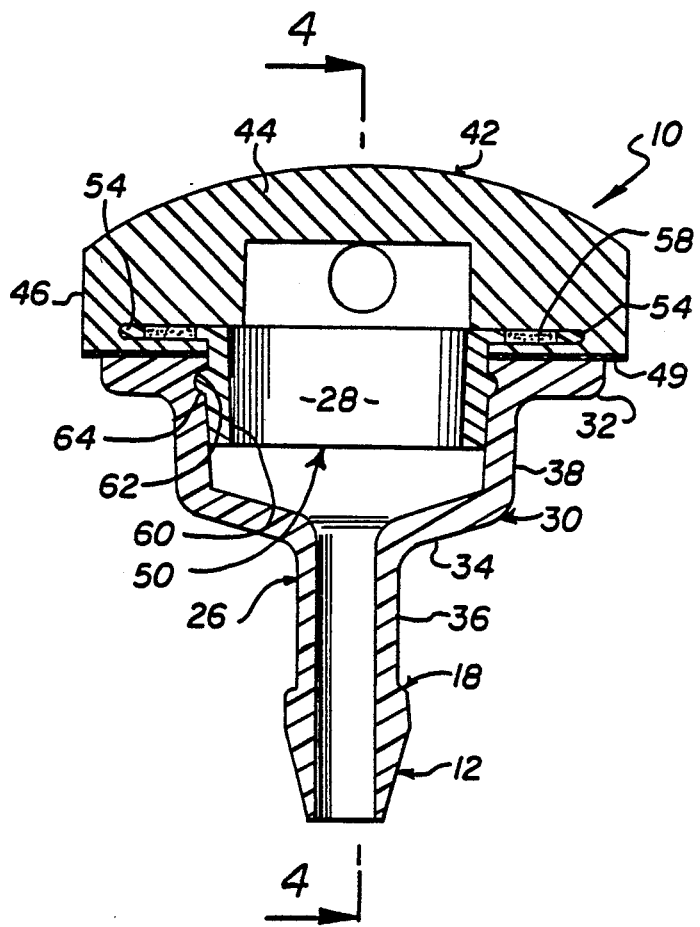
FIG. 3 is an enlarged vertical section taken generally along the line 3—3 of FIG. 1.
Figure 4:
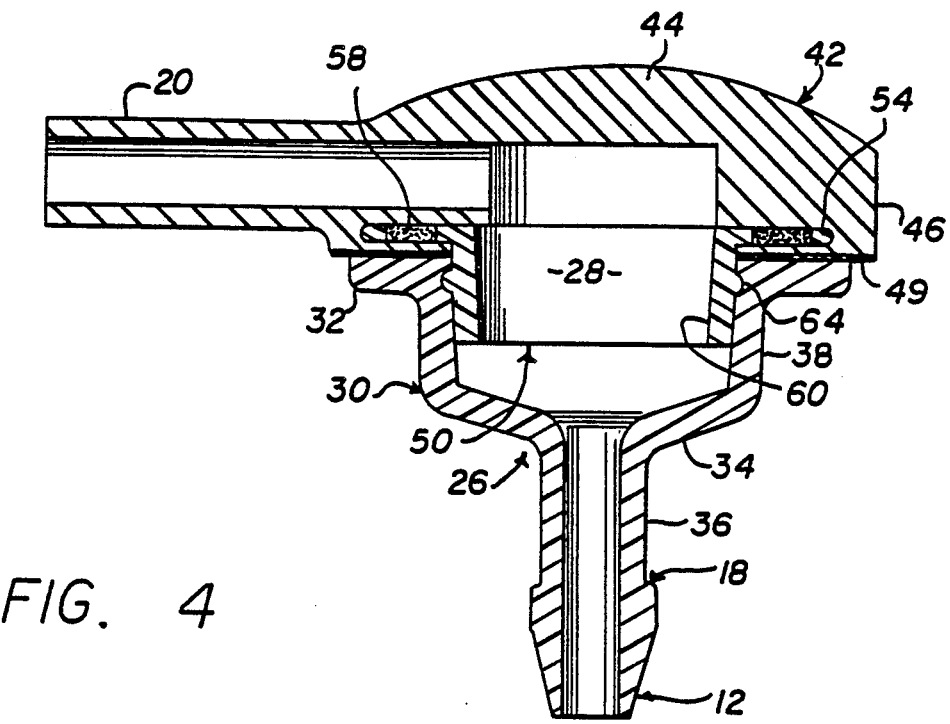
FIG. 4 is a vertical section taken generally along the line 4—4 of FIG. 3.
Figure 6:
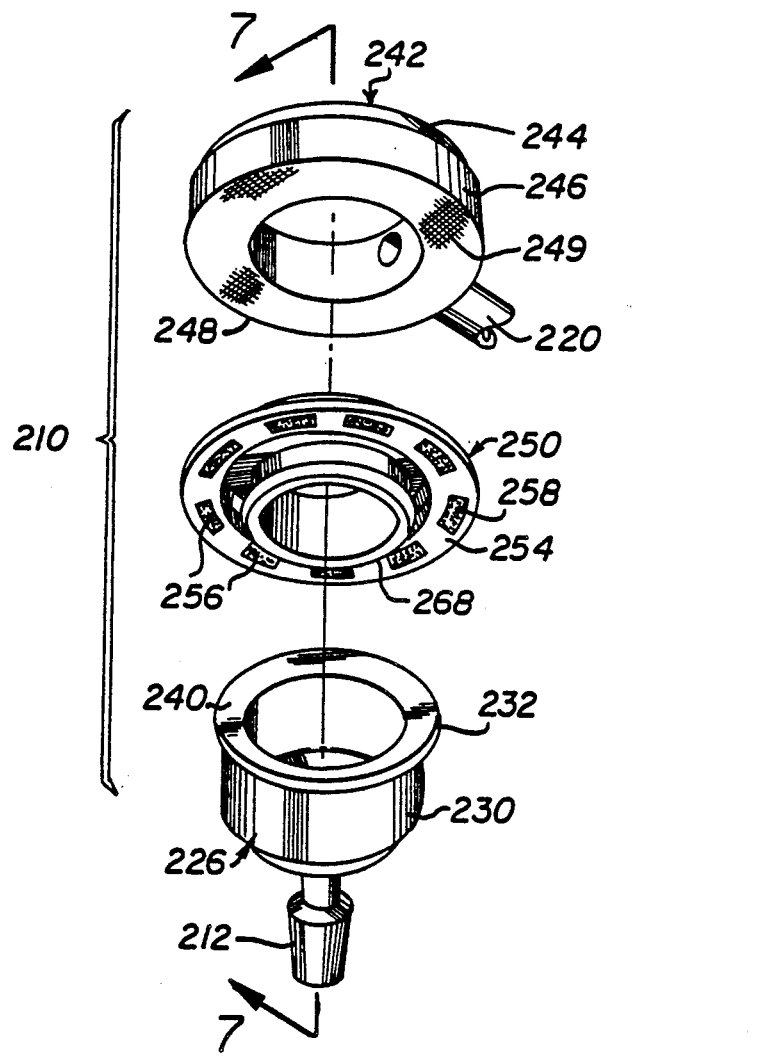
FIG. 6 is an exploded perspective view similar to FIG. 2, of a third embodiment of the ventriculostomy reservoir of the present invention.
Figure 7:
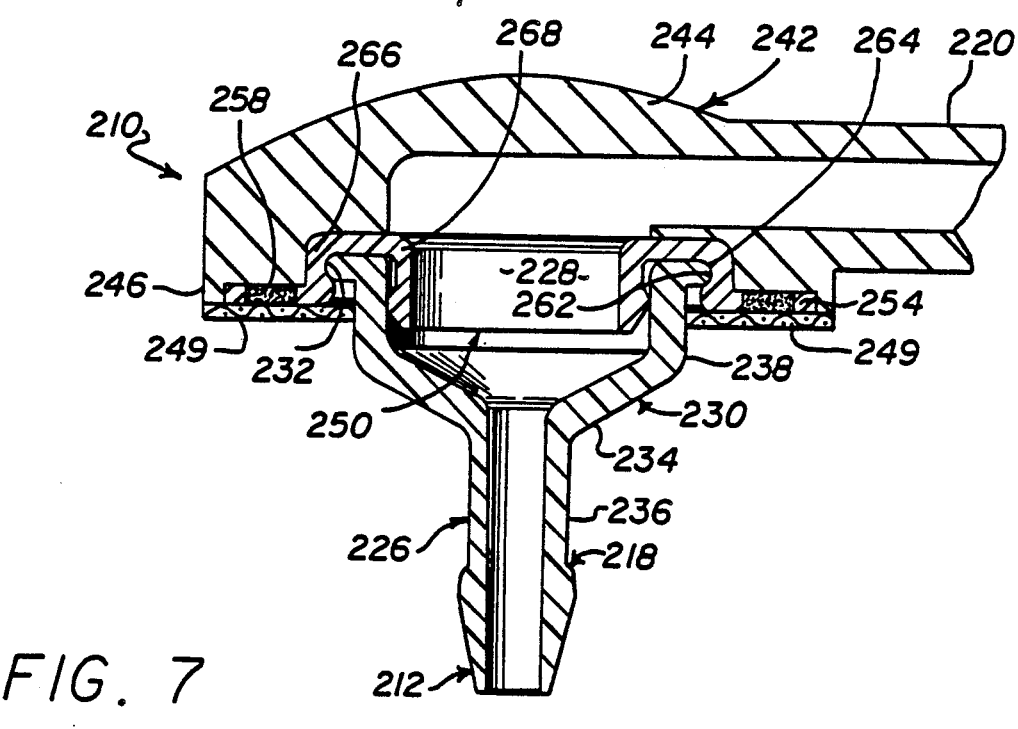
FIG. 7 is a vertical section taken generally along the line 7—7 of FIG. 6, illustrating an assembled configuration of the third embodiment, and particularly the manner in which a cap insert surrounds an upper end of a base to form an interference fit therewith and form a fluid-tight seal.

As shown in the drawings for purposes of illustration, the present invention is concerned with an improved ventriculostomy reservoir, generally designated in FIGS. 1 through 4 by the reference number 10, in FIG. 5 by the reference number 110, and in FIGS. 6 and 7 by the reference number 210. These improved ventriculostomy reservoirs 10, 110 and 210 are intended for use in a surgically implanted shunt system for draining fluid from one portion of the human body to another. In order to connect, for example, the reservoir 10 in such a system, the reservoir includes an inlet connector 12 which receives one end of a piece of surgical tubing or a catheter 14. The inlet tube or catheter 14 slides over the inlet connector 12, and is secured in place by a single ligature 16. The ligature 16 is preferably secured around the catheter 14 just inside of an annular ridge 18 formed near the end of the inlet connector 12. The reservoirs 10, 110 and 210 also include an outlet connector or arm 20 which is dimensioned to receive a straight connector 22 or plug, having an end resembling the inlet connector 12. The outlet connector or arm 20 slides over the straight connector 22, and is secured in place by a single ligature 24 in the same manner that the catheter 14 is secured to the inlet connector 12.

When the reservoirs 10, 110 and 210 are used in a drainage system intended for treatment of hydrocephalus, the inlet connector 12 and the catheter 14 are inserted through the skull into a brain ventricle containing cerebrospinal fluid under pressure. The outlet connector 20 connects to a distal catheter (not shown) which serves to discharge cerebrospinal fluid into, for example, the atrium portion of a patient's heart. A suitable flow control valve, for example either of those illustrated in U.S. Pat. No. 4,560,375, the contents of which are incorporated herein by reference, may be interposed in fluid communication between the reservoir and the distal catheter. Ordinarily, the reservoir will be surgically implanted on the patient's skull with a flap of skin overlying the reservoir.

Although three preferred forms of the invention are illustrated in the accompanying drawings, it is to be understood that each embodiment is the functional equivalent of the other. The reservoirs 110 and 210 shown in FIG. 5 and FIGS. 6 and 7, respectively, simply illustrate alternative designs in comparison with the reservoir 10 illustrated in FIGS. 1 through 4. All three illustrated embodiments of the present invention provide a simplified and highly reliable ventriculostomy reservoir which is designed to facilitate implantation and use thereof by a surgeon. They are each relatively easy to manufacture, are quickly understood and easily assembled during a surgical procedure.

In accordance with the present invention, and as illustrated with respect to the first embodiment in FIGS. 1 through 4, the reservoir 10 includes a relatively rigid, unitized molded plastic base 26 which is formed integrally with the inlet connector 12. The base 26 is configured to provide an internal reservoir well 28, and includes a wall portion 30 which extends upwardly from the inlet connector 12, and a flange portion 32 which is integrally formed with an overlies the wall portion. The wall portion 30 of the base 26 includes a lower frusto-conical section 34 which is formed with a stem 36 of the inlet connector 12, and an intermediate cylindrical section 38 which extends between the flange portion 32 and the frusto-conical section 34. The flange portion 32 includes an upper planar surface 40.

An elastomeric cap 42 is positioned over the base 26 to enclose the reservoir well 28 and define, with the base, an internal reservoir. The cap 42 includes a dome portion 44 which is integrally formed with a peripheral supporting portion 46, and the outlet connector or arm 20. The dome portion 44 is designed to permit injection into the reservoir well 28 by a hypodermic needle. When the cap 42 is placed over the base 26, the base functions as a needle shield to prevent a physician from inadvertently inserting the needle too far, which could puncture the base and extend beyond the limits of the reservoir well 28.

In order to strengthen the cap 42 and facilitate the forming of a fluid-tight seal between the cap and the base 26, the cap is formed with a planar undersurface 48 which faces the flange planar surface 40. Reinforced sheeting 49 is adhesively fixed to the cap planar undersurface 48, and abuts against the flange planar surface 40 to form a seal therebetween. Moreover, a rigid cap insert 50 is positioned within an annular channel 52 provided within the peripheral supporting portion 46 of the cap 42, which cap insert snap-fits into the base 26 to securely hold the cap to the base and also form a fluid-tight seal therebetween.

More particularly, the rigid cap insert 50 includes an annular flange-like portion 54 which is captured within the annular channel 52 of the cap 42. As shown best in FIG. 2, the annular flange-like portion 54 of the cap insert 50 includes a series of apertures 56 which are filled with an adhesive 58. The adhesive 58 tends to secure the annular flange-like portion 54 within the peripheral supporting portion 46 of the cap 42. The cap insert 50 further includes a cylindrical portion 60 which extends downwardly from the flange-portion 54 and fits within the upwardly extending wall portion 30 of the base 26.

In order to snap-fit the cap insert 50 into the base 26, the wall portion 30, and more specifically the cylindrical section 38 of the base, includes an encircling groove or recess 62 on an interior surface thereof, which is adjacent to the cylindrical portion 60 of the cap insert 50 when inserted within the wall portion 30. The cylindrical portion 60 includes an encircling protrusion 64 which is positioned and dimensioned to engage the grove 62 to connect the cap 42 to the base 26.

This protrusion and recess arrangement for connecting the cap 42 to the base 26 enables a physician to quickly and easily assemble the ventriculostomy reservoir 10 during a surgical procedure. During such surgical procedures a catheter 14 is often connected to the inlet connector 12, and then the base 26 is positioned directly over a burr hole through the patient's skull. To complete assembly of the ventriculostomy reservoir 10, the physician only needs to insert the cylindrical portion 60 of the cap insert 50 (which is preassembled with the cap 42), to place the protrusion 64 within the recess 62. This arrangement forms a fluid-tight seal, and eliminates the requirement that the surgeon attempt to manipulate the cap and stretch it over the flange portion 32 of the base 26. In the embodiment of FIGS. 1 through 4, contact between the flange planar surface 40 and the reinforced sheeting 49 attached to the cap planar undersurface 48, tends to create a secondary seal which provides a backup against fluid leakage between the cap 42 and the base 26.

Many of these features are also provided in an alternative second embodiment of the invention, illustrated in FIG. 5, wherein functionally equivalent components common to both embodiments are referred to in the drawings by corresponding reference numbers increased by 100. Again, a rigid base 126 is formed integrally with the inlet connector 112. The base 126 is configured to provide an internal reservoir well 128 and includes an upwardly extending wall portion 130 integrally formed with the inlet connector. More particularly, the wall portion 130 includes a lower frusto-conical section 134 which is formed with a stem 136 of the inlet connector 112. A cylindrical section 138 extends upwardly from the frusto-conical section 134. Unlike the first embodiment described in connection with FIGS. 1 through 4, the embodiment of FIG. 5 does not include a flange portion such as that identified by the reference number 32 in connection with the first illustrated embodiment.

An elastomeric cap 142 is positioned over the base 126 to enclose the reservoir well 128. The cap 142 includes a dome portion 144 which is integrally formed with a peripheral supporting portion 146, and the outlet connector or arm 120. Further, reinforced sheeting 149 is attached to the undersurface of the peripheral supporting portion 146.

In order to connect the cap 142 to the base 126 in a manner forming a fluid-tight seal therebetween, a rigid cap insert 150 is securely positioned within an annular channel 152 provided within the peripheral supporting portion 146 of the cap 142. The cap insert 150 includes an annular flange-like portion 154 which is positioned within the annular channel 152. This annular flange-like portion 154 is nearly identical to that described above in connection with the first embodiment, and includes a plurality of apertures 156 which are filled with an adhesive 158. The purpose of this adhesive 158 is to secure the cap insert 150 within the dome peripheral supporting portion 146.

The ventriculostomy reservoir 110 illustrated in FIG. 5 differs from the embodiment illustrated in FIGS. 1 through 4 primarily in that the annular flange-like portion 154 is positioned within the dome peripheral supporting portion 146 to exteriorly surround an upper end of the base 126. In this regard, an encircling recess 162 is provided on the exterior surface of the wall portion 130 of the base 126 adjacent to the cap insert 150 when the cap 142 is placed over the base 126. The cap insert 150 includes an encircling protrusion 164 which extends inwardly from the annular flange-like portion 154 towards the base 126. The protrusion 164 is configured and dimensioned to engage the recess 162 to connect the cap 142 to the base 126 and form a fluid-tight seal therebetween.

A third embodiment of the invention is illustrated in FIGS. 6 and 7, wherein functionally equivalent components common to the first embodiment illustrated in FIGS. 1 through 4, are referred to in the drawings by corresponding reference numbers increased by 200. The reservoir 210 includes a relatively rigid, unitized molded plastic base 226 which is formed integrally with the inlet connector 212. The base 226 is configured to provide an internal reservoir well 228, and includes a wall portion 230 which extends upwardly from the inlet connector 212, and a flange portion 232 which is integrally formed with and overlies the wall portion. The wall portion 230 of the base 226 includes a lower frusto-conical section 234 which is formed with a stem 236 of the inlet connector 212, and an intermediate cylindrical section 238 which extends between the flange portion 232 and the frusto-conical section 234. The flange portion 232 includes an upper planar surface 240.

An elastomeric cap 242 is positioned over the base 226 to enclose the reservoir well 228 and define, with the base, an internal reservoir. The cap 242 includes a dome portion 244 which is integrally formed with a peripheral supporting portion 246 and an outlet connector or arm 220. The dome portion 244 is designed to permit injection into the reservoir well 228 by a hypodermic needle. When the cap 242 is placed over the base 226, the base functions as a needle shield.

A rigid cap insert 250 is fixed to the cap 242. Like the other cap inserts described above, the cap insert 250 snap-fits over the base 226 to securely hold, by means of an interference fit, the cap to the base and also form a fluid-tight seal therebetween. More particularly, the cap insert 250 includes an annular flange-like portion 254 which is attached to a planar undersurface 248 of the cap 242. This annular flange-like portion 254 is nearly identical to those described above in connection with the first and second embodiments, and includes a plurality of apertures 256 which are filled with an adhesive 258. The purpose of this adhesive 258 is to help secure the cap insert 250 to the dome peripheral supporting portion 246, as well as to support a sheet of reinforced sheeting 249.

The annular flange-like portion 254 of the cap insert 250 is positioned to exteriorly surround an upper end of the base 226. The cap insert 250 has an annular ring-like shape which in cross section resembles a downturned "U". The cap insert 250 overlies the flange portion 232 of the base 226, and includes a first cylindrical portion 266 which encircles the periphery of the base flange portion 232, and a second cylindrical portion 268 which extends downwardly and fits within the upwardly extending wall portion 230 of the base 226.

The first cylindrical portion 266 of the cap insert 250 provides a detent 262 which receives therein the outer periphery of the base flange portion 232. The base flange portion 232 functions as a protrusion 264, in much the same manner as previously described in connection with the first and second embodiments. The second cylindrical portion 268 of the cap insert 250 engages the interior surface of the wall portion 230 to create an interference fit.

As with the other illustrated embodiments, to assemble the ventriculostomy reservoir 220, the physician only needs to snap-fit the cap insert 250 (which is preassembled with the cap 242), over the upper end of the base 226.

From the foregoing, it will be appreciated that the reservoirs 10, 110 and 210 of the present invention provided a device which permits sampling of cerebrospinal fluid flowing directly from the brain ventricle. Each of the ventriculostomy reservoirs 10, 110 and 210 can be fabricated conveniently and economically, are trouble free and reliable in use, and are easily assembled during a surgical procedure.

While three particular forms of the invention have been illustrated and described, it will be apparent that various modifications can be made without departing from the spirit and scope of the invention. Accordingly, it is not intended that the invention be limited, except as by the appended claims.

We claim:

1. A ventriculostomy reservoir, comprising:
a base configured to provide an internal reservoir well, the base including an inlet and an upwardly extending wall portion formed as a unit with the inlet;
a cap positioned over the base to enclose the reservoir well, which cap, together with the base, defines an internal reservoir, the cap including a dome portion, an outlet and a downwardly extending cap ring which engages the base wall portion to hold the cap to the base; and
means for attaching the cap to the base to form a fluid-tight interference fit between the cap and the base, the attaching means including first means associated with the base for connecting the base to the cap, and second means associated with the cap ring for connecting the base to the cap, the first and second connecting means including a detent provided in one of the first and second connecting means, and a protrusion provided on the other of the first and second connecting means, wherein the protrusion and the detent interfit to securely hold the cap to the base.

2. A ventriculostomy reservoir as set forth in claim 1, wherein the base includes a flange portion integrally formed with and overlying the wall portion, the flange portion having an upper planar surface, and wherein the inlet includes an inlet connector which defines an inlet channel.

3. A ventriculostomy reservoir as set forth in claim 2, wherein the outlet includes an outlet arm defining an outlet channel, the outlet arm being integrally formed with the dome, and wherein the dome includes a lower sealing surface which lies against the upper planar surface of the flange portion of the base.

4. A ventriculostomy reservoir as set forth in claim 3, wherein the first connecting means is positioned within the reservoir well, and wherein the second connecting means extends into the well to engage the first connecting means.

5. A ventriculostomy reservoir as set forth in claim 4, wherein the first connecting means comprises the detent, and the second connecting means comprises the protrusion, and wherein the second connecting means includes a cap insert attached to the cap and defining the cap ring, which extends downwardly into the reservoir well.

6. A ventriculostomy reservoir as set forth in claim 5, wherein the cap insert includes a flange captured within a portion of the cap between the dome and the lower sealing surface.

7. A ventriculostomy reservoir as set forth in claim 6, wherein the cap insert flange is secured within the portion of the cap between the dome and the lower sealing surface by means of an adhesive.

8. A ventriculostomy reservoir as set forth in claim 1, wherein the inlet includes an inlet connector which defines an inlet channel, the outlet includes an outlet arm defining an outlet channel, and wherein the outlet arm is integrally formed with the dome.

9. A ventriculostomy reservoir as set forth in claim 1, wherein the first connecting means is incorporated into an exterior surface of the wall portion of the base, and wherein the second connecting means surrounds a portion of the exterior surface of the wall portion of the base to engage the first connecting means.

10. A ventriculostomy reservoir as set forth in claim 9, wherein the first connecting means comprises the detent and the second connecting means comprises the protrusion, and wherein the second connecting means includes a separable cap insert attached to the cap, the separable cap insert forming the cap ring.

11. A ventriculostomy reservoir as set forth in claim 10, wherein the cap insert includes an annular flange-like portion attached to the cap by means of an adhesive.

12. A ventriculostomy reservoir as set forth in claim 1, wherein the first connecting means includes a base flange integrally formed with and overlying the wall portion of the base to provide the protrusion, and wherein the second connecting means includes a cap insert attached to the cap to provide the cap ring, which cap insert is mated to the base flange in an interference fit.

13. A ventriculostomy reservoir as set forth in claim 12, wherein the cap insert is configured to exteriorly surround the base flange, and provides the detent which receives the protrusion provided by the base flange.

14. A ventriculostomy reservoir as set forth in claim 12, wherein the cap insert overlies the base flange and includes means extending into the reservoir well for engaging an interior surface of the wall portion of the base.

15. A ventriculostomy reservoir as set forth in claim 14, wherein the cap insert includes an annular flange-like portion attached to the cap by means of an adhesive.

16. A ventriculostomy reservoir, comprising:
a rigid base configured to provide an internal reservoir well, the base including a catheter connector defining a reservoir inlet, an upwardly extending wall portion integrally formed with the catheter connector, and first means for connecting a cap to the base to form a fluid-tight seal therebetween;
an elastomeric cap positioned over the base to enclose the reservoir well and define, with the base, an internal reservoir, the cap including a dome portion integrally formed with a peripheral supporting portion, and an outlet; and
a rigid cap insert securely affixed to the cap and positioned for engagement with the base, the cap insert including second means for connecting the cap to the base to form a fluid-tight seal therebetween, wherein said seal between the cap and the base is formed as the first and second connecting means engage one another.

17. A ventriculostomy reservoir as set forth in claim 16, wherein the cap insert includes an annular flange-like portion which is supported by the dome peripheral supporting portion.

18. A ventriculostomy reservoir as set forth in claim 17, wherein the annular flange-like portion of the cap insert includes a plurality of apertures filled with an adhesive.

19. A ventriculostomy reservoir as set forth in claim 17, wherein the cap insert includes a cylindrical portion which extends downwardly from the annular flange-like portion, which cylindrical portion engages an interior surface of the upwardly extending wall portion of the base in an interference fit.

20. A ventriculostomy reservoir as set forth in claim 19, wherein the first connecting means includes an encircling detent on the interior surface of the wall portion of the base adjacent to the cylindrical portion of the cap insert, and the second connecting means includes an encircling protrusion on an exterior surface of the cylindrical portion of the cap insert, wherein the protrusion engages the detent to connect the cap to the base.

21. A ventriculostomy reservoir as set forth in claim 20, wherein the base includes a flange portion integrally formed with and overlying the wall portion, the flange portion having a upper planar surface, and wherein the cap includes a lower sealing surface which lies against the upper planar surface of the flange portion of the base.

22. A ventriculostomy reservoir as set forth in claim 17, wherein the annular flange-like portion is positioned within the dome peripheral supporting portion to exteriorly surround an upper end of the base.

23. A ventriculostomy reservoir as set forth in claim 22, wherein the first connecting means includes an encircling detent on an exterior surface of the wall portion of the base adjacent to the cap insert, and the second connecting means includes an encircling protrusion provided on an interior surface of the cap insert, wherein the protrusion engages the detent to connect the cap to the base.

24. A ventriculostomy reservoir as set forth in claim 16, wherein the first connecting means includes an encircling protrusion on an exterior surface of the wall portion of the base adjacent to the cap insert, and wherein the second connecting means includes an encircling detent provided on an interior surface of the cap insert, wherein the protrusion engages the detent in an interference fit to connect the cap to the base.

25. A ventriculostomy reservoir as set forth in claim 16, wherein the cap insert overlies the base and includes means extending into the reservoir well for engaging an interior surface of the wall portion of the base in an interference fit.

26. A ventriculostomy reservoir as set forth in claim 16, including reinforced sheeting means attached to the dome peripheral supporting portion, for minimizing elastic stretching of the dome peripheral supporting portion.

27. A ventriculostomy reservoir, comprising:
a rigid base configured to provide an internal reservoir well, the base including a catheter connector defining a reservoir inlet, an upwardly extending wall portion integrally formed with the catheter connector, a flange portion integrally formed with and overlying the wall portion, wherein the flange portion includes an upper planar surface, and an encircling detent on an interior surface of the wall portion of the base;
an elastomeric cap positioned over the base to enclose the reservoir well and define, with the base, an internal reservoir, the cap including a dome portion integrally formed with a peripheral supporting portion, and an outlet including an outlet arm which defines an outlet channel, the outlet arm being integrally formed with the dome, wherein the dome includes a lower sealing surface which lies in an abutting relation to the upper planar surface of the flange portion of the base; and
a rigid cap insert including an annular flange-like portion which is captured within the dome peripheral supporting portion, and a cylindrical portion which extends downwardly from the annular flange-like portion, the annular flange-like portion of the cap insert including a plurality of apertures filled with an adhesive which secures the cap insert within the dome peripheral supporting portion, and wherein the cylindrical portion is configured to fit within the upwardly extending wall portion of the base, the cylindrical portion including an encircling protrusion on an exterior surface thereof which engages the detent to connect the cap to the base and form a fluid-tight seal therebetween.

28. A ventriculostomy reservoir, comprising:
a rigid base configured to provide an internal reservoir well, the base including a catheter connector defining a reservoir inlet, an upwardly extending wall portion integrally formed with the catheter connector, and an encircling detent on an exterior surface of the wall portion of the base;
an elastomeric cap positioned over the base to enclose the reservoir well and define, with the base, an internal reservoir, the cap including a dome portion integrally formed with a peripheral supporting portion, and an outlet including an outlet arm defining an outlet channel, wherein the outlet arm is integrally formed with the dome; and
a rigid cap insert including an annular flange-like portion which is captured within the dome peripheral supporting portion, wherein the annular flange-like portion includes a plurality of apertures filled with an adhesive which secures the cap insert within the dome peripheral supporting portion, the cap insert being positioned by the dome to exteriorly surround an upper end of the base, wherein the cap insert further includes an encircling protrusion which extends from the annular flange-like portion inwardly toward the wall portion of the base, wherein the protrusion engages the detent to connect the cap to the base and form a fluid-tight seal therebetween.

29. A ventriculostomy reservoir, comprising:
a rigid base configured to provide an internal reservoir well, the base including a catheter connector defining a reservoir inlet, an upwardly extending wall portion integrally formed with the catheter connector, and a flange portion integrally formed with and overlying the wall portion;
an elastomeric cap positioned over the base to enclose the reservoir well and define, with the base, an internal reservoir, the cap including a dome portion integrally formed with a peripheral supporting portion, and an outlet including an outlet arm which defines an outlet channel, the outlet arm being integrally formed with the dome; and
a rigid cap insert including an annular flange-like portion which is attached to the dome peripheral supporting portion, wherein the annular flange-like portion includes a plurality of apertures filled with an adhesive which secures the cap insert to the dome peripheral supporting portion, the cap insert being positioned by the dome to exteriorly surround the flange portion of the base, and providing a detent which receives a peripheral edge of the base flange, and wherein the cap insert overlies the base flange and includes means extending into the reservoir well for engaging an interior surface of the wall portion of the base to connect the cap to the base by means of an interference fit and form a fluid-tight seal therebetween.

30. A ventriculostomy reservoir, comprising:
a base configured to provide an internal reservoir well;
a cap positioned over the base to enclose the reservoir well, which cap, together with the base, defines an internal reservoir;
a rigid cap insert securely affixed to the cap and positioned for engagement with the base;
an inlet to the internal reservoir;
an outlet from the internal reservoir; and
means for attaching the cap to the base including first means associated with the base for connecting the base to the cap, and second means associated with the cap insert for connecting the base to the cap, wherein the first and second connecting means interfit to securely hold the cap to the base by means of an interference fit and form a fluid-tight seal therebetween.

31. A ventriculostomy reservoir as set forth in claim 30, wherein the cap insert includes a portion which extends downwardly from the cap for engagement with an interior surface of the reservoir well in an interference fit.

32. A ventriculostomy reservoir as set forth in claim 30 wherein the first and second connecting means include a detent provided in one of the first and second connecting means, and a protrusion provided on the other of the first and second connecting means, wherein the protrusion and the detent interfit to securely hold the cap to the base.

33. A ventriculostomy reservoir as set forth in claim 31, wherein the first connecting means includes an encircling detent on the interior surface of the reservoir well, and the second connecting means includes an encircling protrusion on an exterior surface of the portion of the cap insert extending downwardly from the cap, wherein the protrusion engages the detent to connect the cap to the base.

34. A ventriculostomy reservoir as set forth in claim 30, wherein the cap insert includes a portion which extends from the cap for engagement with an exterior surface of the base in an interference fit.

35. A ventriculostomy reservoir as set forth in claim 34, wherein the first and second connecting means include a detent provided in one of the first and second connecting means, and a protrusion provided on the other of the first and second connecting means, wherein the protrusion and the detent interfit to securely hold the cap to the base.

* * * * *